(12) United States Patent
Merli et al.

(10) Patent No.: US 7,166,721 B2
(45) Date of Patent: *Jan. 23, 2007

(54) PREPARATION OF 1H-IMIDAZO[4,5-C] QUINOLIN 4-AMINES VIA NOVEL 1H-IMIDAZO[4,5-C] QUINOLIN 4-CYANO AND 1H-IMIDAZO[4,5-C] QUINOLIN 4-CARBOXAMIDE INTERMEDIATES

(75) Inventors: Valeriano Merli, Cremella Lecco (IT); Silvia Mantovani, Lendinara (IT); Stefano Bianchi, Breccia Como (IT)

(73) Assignee: TEVA Gyógyszergyár Zártkörűen Működő Részvénytársaság, Debrecen (HU)

( * ) Notice: Subject to any disclaimer, the term of this patent is extended or adjusted under 35 U.S.C. 154(b) by 0 days.

This patent is subject to a terminal disclaimer.

(21) Appl. No.: 11/009,259

(22) Filed: Dec. 9, 2004

(65) Prior Publication Data

US 2005/0101627 A1    May 12, 2005

Related U.S. Application Data

(62) Division of application No. 10/628,927, filed on Jul. 28, 2003, now Pat. No. 6,841,678.

(60) Provisional application No. 60/398,592, filed on Jul. 26, 2002.

(51) Int. Cl.
  *C07D 471/06*  (2006.01)
  *C07D 471/02*  (2006.01)
(52) U.S. Cl. .............................. 546/82; 546/80; 546/79
(58) Field of Classification Search ................. 546/82, 546/80, 79
See application file for complete search history.

(56) References Cited

U.S. PATENT DOCUMENTS

| | | | | |
|---|---|---|---|---|
| 4,689,338 A | 8/1987 | Gerster | ....................... | 514/293 |
| 4,689,388 A | 8/1987 | Hirai et al. | ................. | 528/104 |
| 4,698,348 A | 10/1987 | Gerster | ....................... | 514/293 |
| 4,988,815 A | 1/1991 | Andréet al. | ................. | 546/159 |
| 5,238,944 A | 8/1993 | Wick et al. | .................. | 514/293 |
| 5,367,076 A | 11/1994 | Gerster | ........................ | 546/82 |
| 5,395,937 A | 3/1995 | Nikolaides et al. | ........... | 546/82 |
| 5,578,727 A | 11/1996 | Andre et al. | .................. | 546/82 |
| 5,602,256 A | 2/1997 | Andréet al. | ................. | 546/180 |
| 5,756,747 A | 5/1998 | Gerster | ........................ | 546/82 |
| 6,841,678 B1 * | 1/2005 | Merli et al. | ................... | 546/82 |

FOREIGN PATENT DOCUMENTS

| | | |
|---|---|---|
| EP | 0 145 340 A2 | 6/1985 |
| EP | 0 145 340 B1 | 6/1985 |
| EP | 0 310 950 A1 | 4/1989 |
| EP | 0 310 950 B1 | 4/1989 |
| EP | 0 385 630 A2 | 9/1990 |
| EP | 0 385 630 A3 | 9/1990 |
| EP | 0 385 630 B1 | 9/1990 |
| EP | 1256582 | 11/2002 |
| JP | 4-193866 | 7/1992 |
| WO | WO 92/06093 | 4/1992 |
| WO | WO 92/15581 | 9/1992 |
| WO | WO 97/48704 | 12/1997 |
| WO | WO 01/58900 A1 | 8/2001 |
| WO | WO 03/097641 | * 11/2003 |

OTHER PUBLICATIONS

R.T. Morrison et al., NY University, "Organic Chemistry, 6th Ed." p. 838-843, (1992) Prentice Hall, New Jersey.
R.C. Elderfield, University of Michigan, "Heterocyclic Compounds", vol. 4, Quinoline, Isoquinoline, and Their Benzo Derivatives, New York—John Wiley & Sons, Inc., London—Chapman & Hall, Limited, p. 243 (1952).

* cited by examiner

*Primary Examiner*—Charanjit S. Aulakh
(74) *Attorney, Agent, or Firm*—Kenyon & Kenyon LLP

(57) ABSTRACT

The invention relates to a process for the synthesis of 1H-imidazo[4,5-c] quinoline 4-cyano and 1H-imidazo[4,5-c]quinoline 4-carboxamide intermediates useful in preparing 1H-imidazo[4,5-C] quinoline 4-amines, a process for preparing 1H-imidazo[4,5-C] quinoline 4-amines using such intermediates; and, to the 1H-imidazo[4,5-c] quinoline 4-cyano and 1H-imidazo[4,5-c] quinoline 4-carboxamide intermediates. More particularly, the invention relates to a process for the preparation of 1-isobutyl-1H-imidazo[4,5-C] quinoline 4-amine (Imiquimod) using two intermediates, 1-isobutyl-1H-imidazo[4,5-c] quinoline 4-cyano and 1-isobutyl-1H-imidazo[4,5-c] quinoline 4-carboxamide, and to the said intermediates.

14 Claims, 4 Drawing Sheets

PREPARATION OF 1H-IMIDAZO[4,5-C] QUINOLIN 4-AMINES VIA NOVEL 1H-IMIDAZO[4,5-C] QUINOLIN 4-CYANO AND 1H-IMIDAZO[4,5-C] QUINOLIN 4-CARBOXAMIDE INTERMEDIATES

CROSS-REFERENCE TO RELATED APPLICATION

This application is a divisional of U.S. patent application Ser. No. 10/628,927, filed Jul. 28, 2003 now U.S. Pat. No. 6,841,678, which claims the benefit of provisional application Ser. No. 60/398,592, filed Jul. 26, 2002, which is incorporated herein by reference.

FIELD OF THE INVENTION

The invention relates to a process for the synthesis of 1H-imidazo[4,5-c]quinoline 4-cyano and 1H-imidazo[4,5-c]quinoline 4-carboxamide intermediates useful in preparing 1H-imidazo[4,5-C]quinoline 4-amines, a process for preparing 1H-imidazo[4,5-C]quinoline 4-amines using such intermediates; and, to the 1H-imidazo[4,5-c]quinoline 4-cyano and 1H-imidazo[4,5-c]quinoline 4-carboxamide intermediates. More particularly, the invention relates to a process for the preparation of 1-isobutyl-1H-imidazo[4,5-C]quinoline 4-amine (Imiquimod) using two intermediates, 1-isobutyl-1H-imidazo[4,5-c] quinoline 4-cyano and 1-isobutyl-1H-imidazo[4,5-c]quinoline 4-carboxamide, and to the said intermediates.

BACKGROUND OF THE INVENTION

Imiquimod, 1-isobutyl-1H-imidazo[4,5-C]quinolin-4-amine, is an immune response modifier, useful for treating viral infections, such as genital warts. Imiquimod is disclosed in U.S. Pat. Nos. 4,689,338 and 5,238,944 and has the structure:

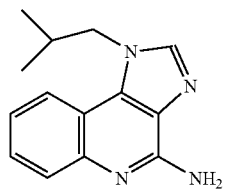

Several methods are known in the art for making 1H-imidazo[4,5-c]quinoline 4-amines, including Imiquimod. The amino group in the 4 position has been introduced in essentially three ways: The first is by nucleophilic substitution of a leaving group, e.g., Cl, triflate, etc., with ammonia, dibenzylamine or an azido group; the second is by reacting 1-isobutyl-1H-imidazo[4,5-c]quinoline-N-oxide with ammonium hydroxide or ammonium salts in the presence of tosyl chloride at 0–5° C.; and the third is by reacting 1-isobutyl-1H-imidazo[4,5-c]quinoline-N-oxide with benzoyl isocyanate.

Nucleophilic substitution reactions are disclosed in, for example, WO 97/48704, WO 92/06093, U.S. Pat. Nos. 5,395,937, 5,756,747, 4,988,815, 5,602,256, 5,578,727, 4,698,348, 4,689,388, European patents EP 145340, EP 0385630, EP 310950 and JP 04193866. Specifically, in WO 97/48704 the amino group is introduced by reaction of a 4-chloro derivative with sodium azide to obtain a tetrazole moiety. Reaction of the tetrazole moiety with triphenylphosphine gives the 4-amino derivative. In U.S. Pat. No. 5,395,937, a 4-triflate derivative is reacted with dibenzylamine. The catalytic reduction of the 4-dibenzylamino derivative places an amino group in the 4-position. U.S. Pat. No. 5,756,474, discloses a nucleophilic substitution with ammonia on a 4-chloro derivative, obtained by isomerization of 1-isobutyl-1H-imidazo[4,5-c]quinoline-N-oxide to the 4-hydroxy derivative, followed by reaction with POCl$_3$. The following patents all disclose a nucleophilic substitution of 1-isobutyl-1H-imidazo[4,5-c]quinoline-4-chloro with ammonia at high temperature and pressure: U.S. Pat. Nos. 4,988,815, 5,602256, 5,578,727, 4,698,348, 4,689,388, EP 145340, JP 04193866, EP 0385630, and EP 310950.

WO 92/06093 discloses reacting 1-isobutyl-1H-imidazo[4,5-c]quinoline-N-oxide with ammonium hydroxide or ammonium salts in the presence of tosyl chloride at 0–5° C.

WO 92/15581 discloses reacting 1-isobutyl-1H-imidazo[4,5-c]quinoline-N-oxide with benzoyl isocyanate.

However, a need exists in the art for making 1H-imidazo[4,5-C]quinoline 4-amines, especially Imiquimod, in high purity and high yield and which does not require high temperature or pressure.

SUMMARY OF THE INVENTION

Figure 1:
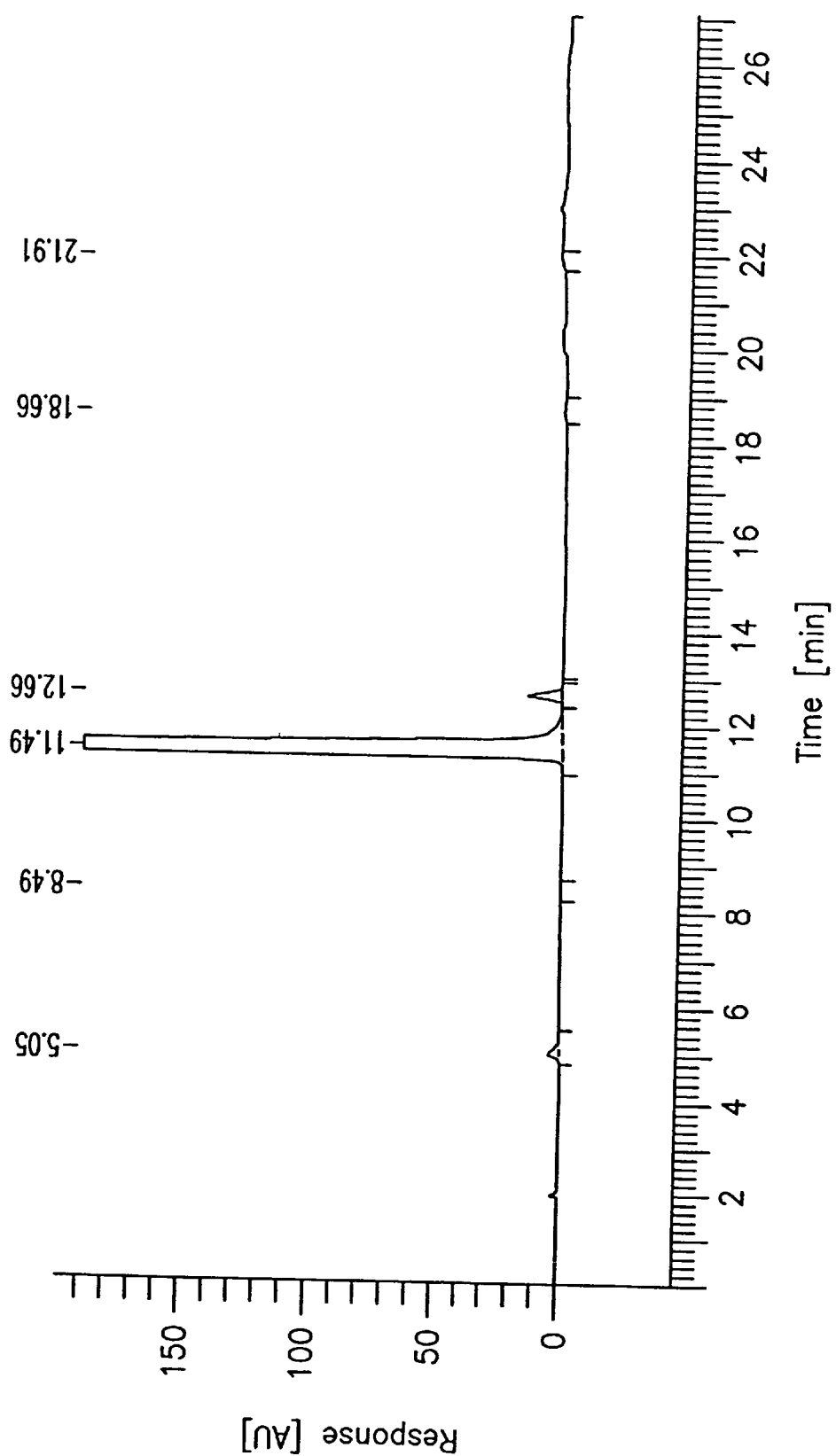
FIGS. 1–4 are chromatograms of the solid 1-isobutyl-1H-imidazo[4,5-c]quinoline-4-carboxamide made according to the invention.
Figure 2:
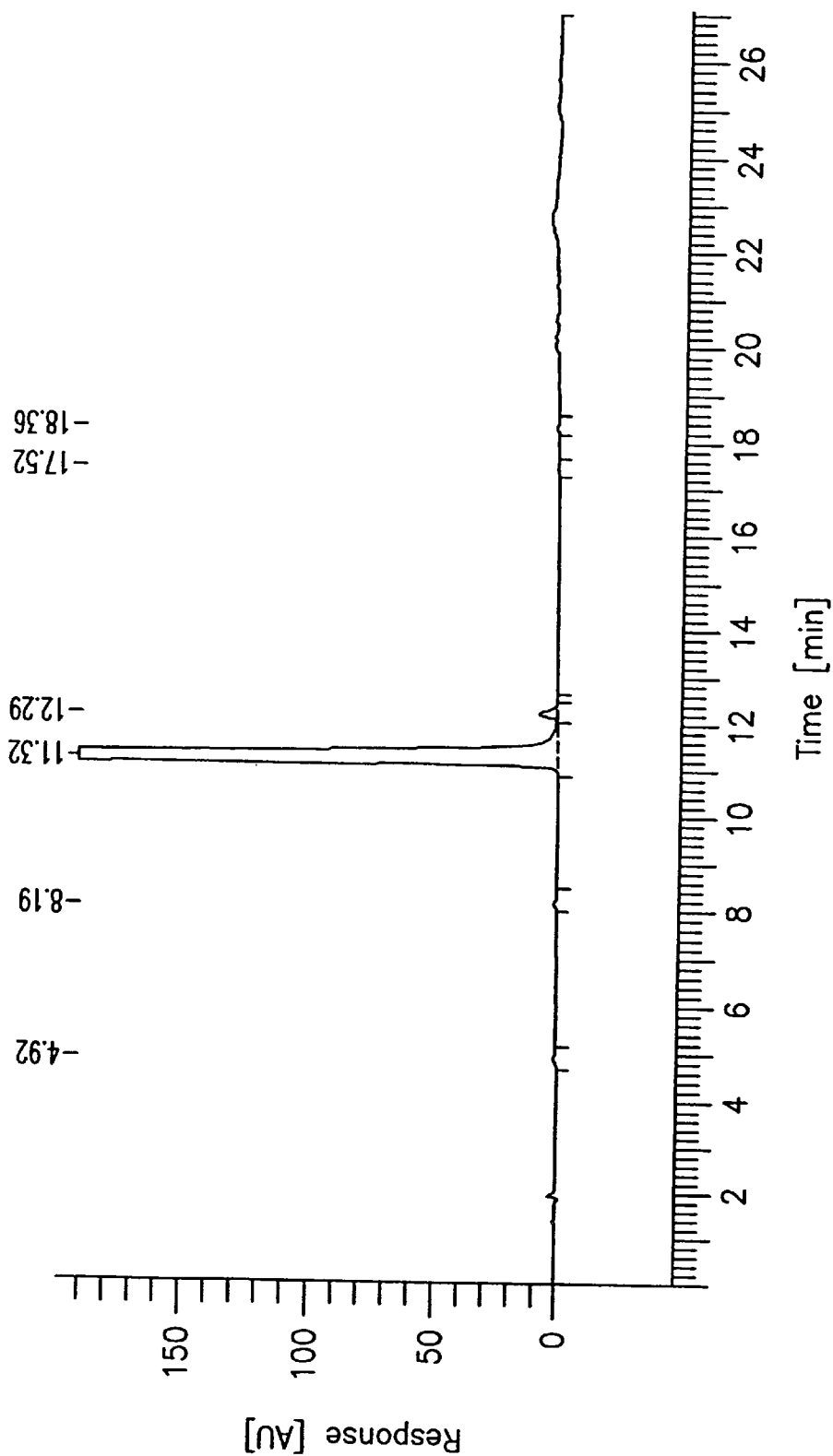
Figure 3:
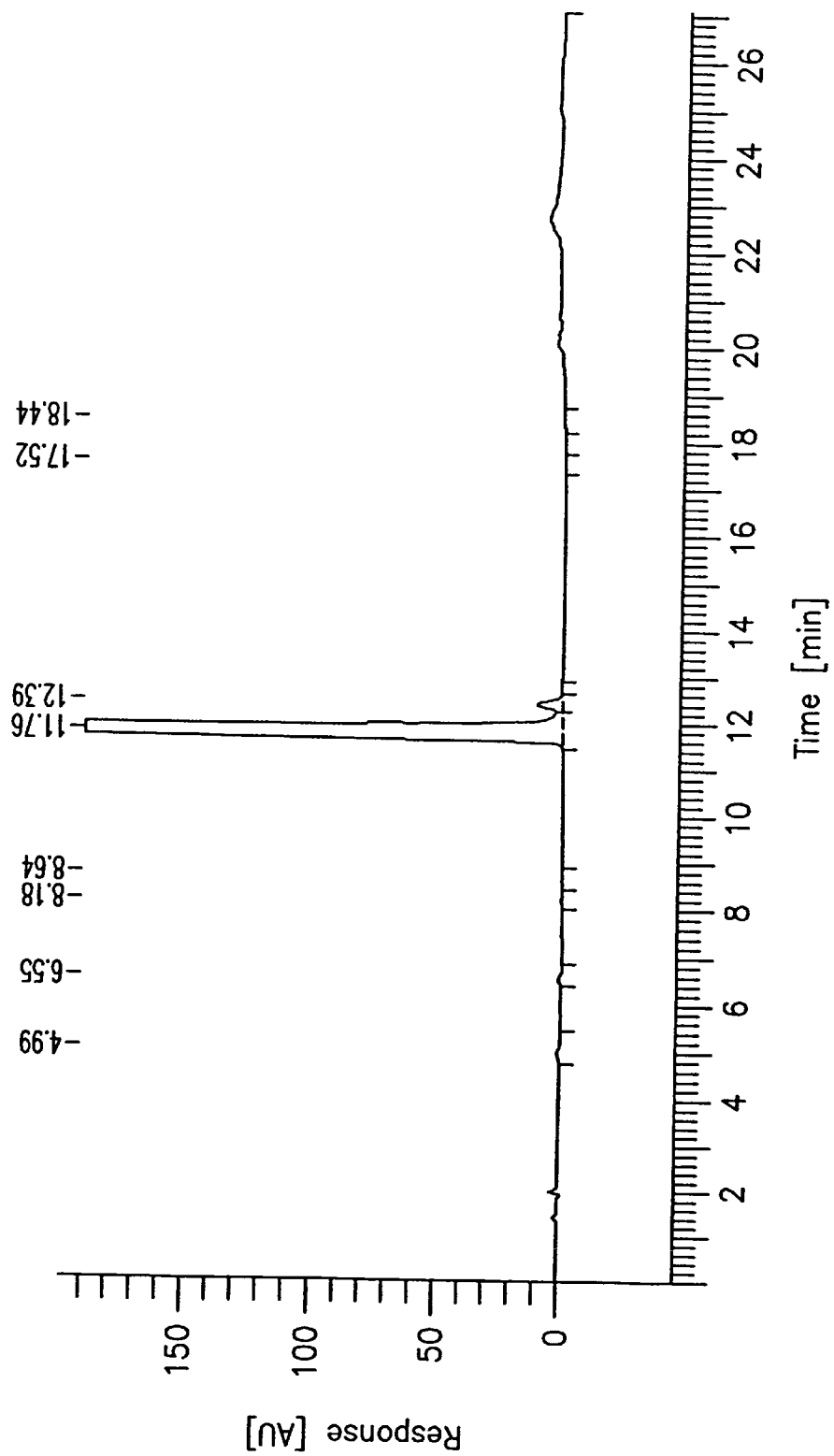
Figure 4:
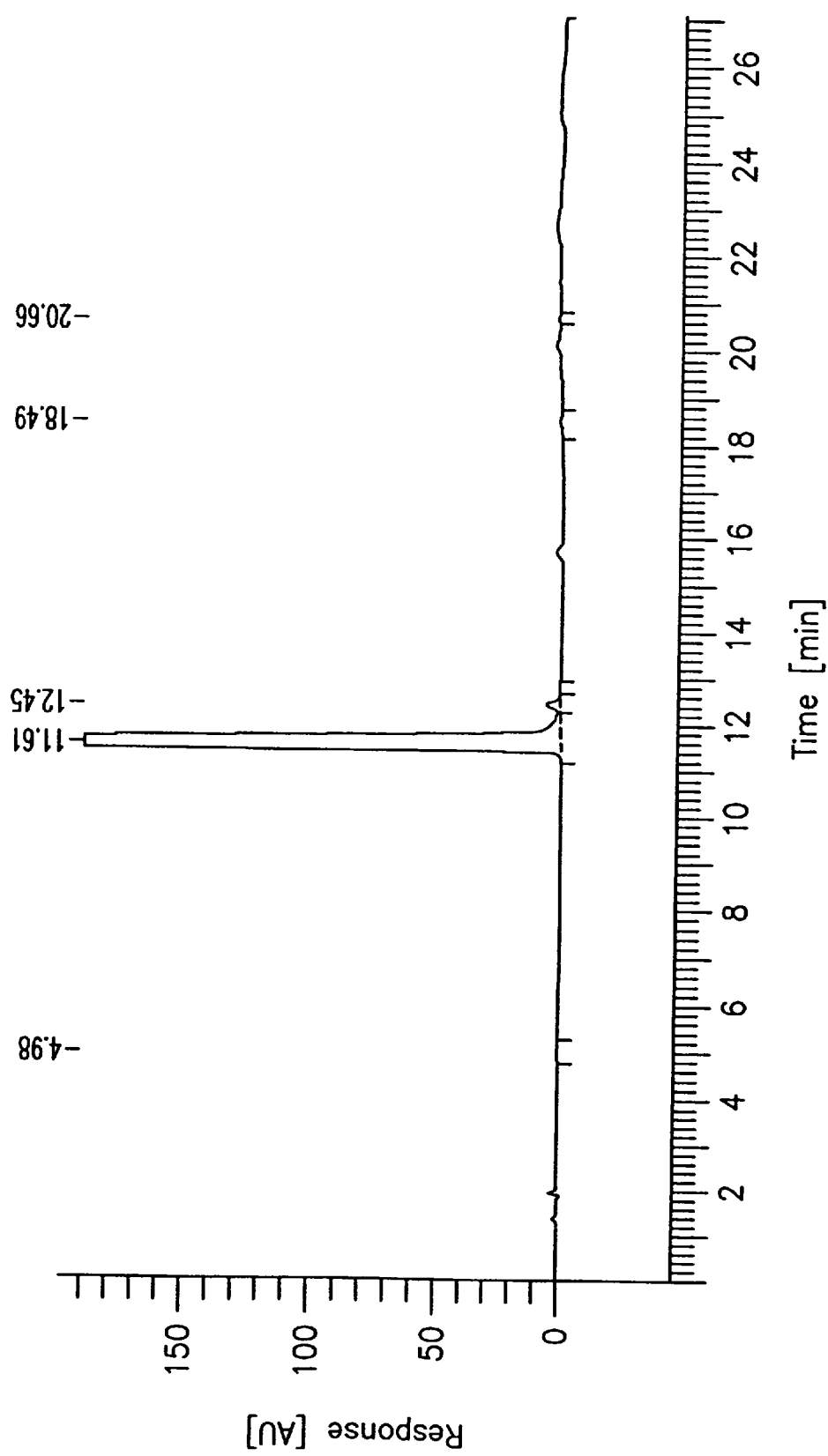

In one aspect, the present invention is directed to a compound of formula (II) and salts thereof:

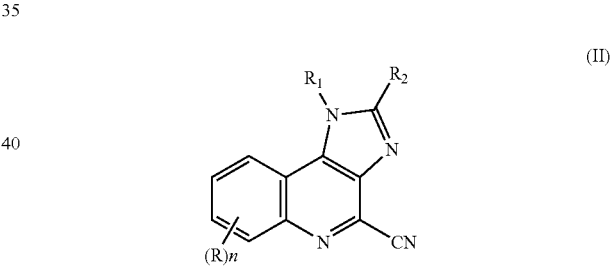

wherein

R$_1$ is selected from the group consisting of: hydrogen; a straight or branched chain alkyl of one to about 10 carbon atoms, optionally substituted with a substituent selected from the group consisting of lower alkyl, cycloalkyl of 3 to about 6 carbon atoms, wherein said cycloalkyl is optionally substituted with a lower alkyl group; straight or branched chain alkenyl of 2 to about 10 carbon atoms, wherein the olefinic unsaturation in the alkenyl group is at least one carbon atom removed from the 1-nitrogen, and wherein the straight or branched chain alkyl is optionally substituted with a substituent selected from the group consisting of lower alkyl, cycloalkyl of 3 to about 6 carbon atoms, wherein said cycloalkyl is optionally substituted with a lower alkyl group; hydroxyalkyl of one to about six carbon atoms; acyloxyalkyl wherein the acyloxy moiety is alkanoyloxy of two to about four carbon atoms or benzoyloxy and the alkyl moiety contains one to about six carbon atoms; benzyl; (phenyl)ethyl; and phenyl, wherein said benzyl, (phenyl)ethyl and phenyl substituents are optionally substituted on the benzene ring by one or two moieties independently selected from the group consisting of lower alkyl, lower alkoxy, and halogen, with the proviso that when the benzene ring is substituted by two such moieties, then the moieties together contain more than 6 carbon atoms;

$R_2$ is selected from the group consisting of: hydrogen; straight or branched chain alkyl containing one to about eight carbon atoms; benzyl; (phenyl)ethyl; and phenyl, wherein said benzyl, (phenyl)ethyl and phenyl substituents are optionally substituted on the benzene ring by one or two moieties independently selected from the group consisting of lower alkyl, lower alkoxy, and halogen, with the proviso that when the benzene ring is substituted by two such moieties, then the moieties together contain more than 6 carbon atoms;

R is independently selected from the group consisting of: alkoxy of one to about four carbon atoms; alkyl of one to about four carbon atoms; and halogen; and n is an integer from 0 to 2, with the proviso that if n is 2, then said groups together contain no more than 6 carbon atoms.

In a preferred embodiment, $R_1$ is isobutyl, $R_2$ is hydrogen, and n is 0.

In another aspect, the present invention is directed to a process for preparing a 1H-imidazo[4,5-c]quinoline 4-cyano compound of formula (II) and salts thereof, comprising reacting a compound of formula (III) with an alkali metal cyanide, wherein R, $R_1$, $R_2$ and n are defined above.

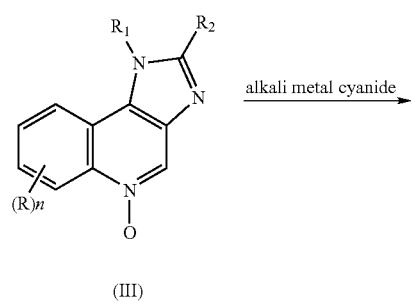

(III)

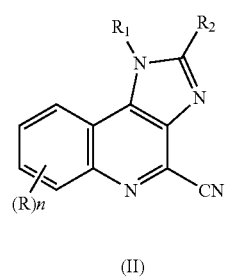

(II)

In another aspect, the invention is directed to a compound of formula (IV) and salts thereof:

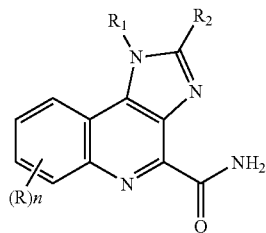

(IV)

wherein R, $R_1$, $R_2$ and n are defined above. In a preferred embodiment, $R_1$ is isobutyl, $R_2$ is hydrogen, and n is 0.

In another aspect, the invention is directed to a process for preparing a compound of formula (IV) and salts thereof, comprising reacting a compound of formula (II) with an aqueous solution of a strong acid.

In another aspect, the present invention is directed to a process for preparing a compound of formula (I) or a pharmaceutically acceptable acid addition salt thereof:

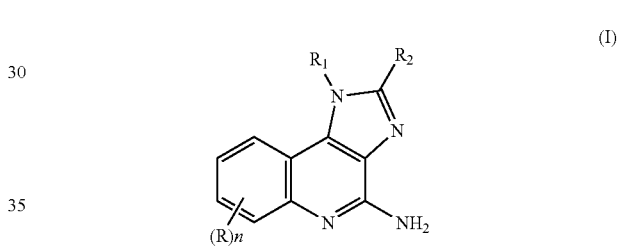

(I)

wherein R, $R_1$, $R_2$ and n are defined above, comprising subjecting a compound of formula (IV) or a salt thereof, to a Hofmann rearrangement or degradation reaction. In a preferred embodiment, $R_1$ is isobutyl, $R_2$ is hydrogen, and n is 0.

These and other aspects of the present invention will now be described in more detail with reference to the following detailed description of the invention.

DETAILED DESCRIPTION OF THE INVENTION

In one aspect, the present invention is directed to a process for preparing 1H-imidazo[4,5-c]quinoline-4-amines of formula (I). The preferred 1H-imidazo[4,5-c]quinoline-4-amine is Imiquimod. However, the inventive process can be used to prepare any compound within the scope of formula (I), including those disclosed in U.S. Pat. Nos. 5,756,747, 5,395,937, 4,689,338, EP 385630, WO 97/48704, WO 92/06093 and WO 92/15581, all of which are incorporated by reference in their entirety herein.

The invention is also directed to novel 1H-imidazo[4,5-c]quinoline 4-cyano intermediates of formula (II) and 1H-imidazo[4,5-c]quinoline 4-carboxamide intermediates of formula (IV), which are useful in preparing 1H-imidazo

[4,5-c]quinoline-4-amines of formula (I), and to a process for preparing the intermediates of formula (II) and formula (IV). The preferred intermediates are 1-isobutyl-1H-imidazo[4,5-c]quinoline 4-cyano and 1-isobutyl-1H-imidazo[4,5-c]quinoline 4-carboxamide.

The 1H-imidazo[4,5-c]quinoline 4-cyano intermediates of formula (II) are prepared by reacting a 1H-imidazo[4,5-c]quinoline N-oxide of formula (III) with an alkali metal cyanide, such as sodium cyanide. The 1H-imidazo[4,5-c]quinoline N-oxides of formula (III) can be obtained by any method known in the art, including those disclosed in: U.S. Pat. No. 5,756,747, WO 92/06093 and WO 92/15581, all of which are incorporated by reference in their entirety herein.

The reaction between quinoline N-oxide and nucleophiles has been reported in Elderfield, *Heterocyclic Compounds*, Vol. 4, p 243. The reaction between 1H-imidazo[4,5-c]quinoline N-oxide of formula (III) and alkali metal cyanide is preferably carried out in the presence of an organic acid halide, such as, benzoyl chloride and a suitable solvent. A large excess, i.e., a 3:1 molar ratio, of alkali metal cyanide may be used to minimize formation of the 1H-imidazo[4,5-c]quinoline-4-hydroxy derivative. A preferred solvent is a mixture of methylene chloride and water. The reaction is preferably carried out at a temperature of between about −5 to 5° C., more preferably between about −5 to −1° C., and most preferably at about 0° C. The organic acid halide is preferably added over a period of about 1 to 3 hours, more preferably from about 1 to 2 hours and most preferably for about 1 hour and 40 minutes. The reaction is complete when no 1H-imidazo[4,5-c]quinoline N-oxide is detected by HPLC. It is not necessary to isolate the 1H-imidazo[4,5-c]quinoline 4-cyano compound to make the 1H-imidazo[4,5-c]quinoline 4-carboxamide intermediate. When the reaction is complete, the phases are separated and the organic layer containing the 1H-imidazo[4,5-c]quinoline 4-cyano compound is washed and concentrated. Tetrabutyl ammonium bromide may be added to obtain good phase separation.

To prepare a 1H-imidazo[4,5-c]quinoline 4-carboxamide intermediate of formula (IV), a 1H-imidazo[4,5-c]quinoline 4-cyano intermediate of formula (II) is reacted with a hot aqueous solution of a strong acid. Preferably, a 30% hydrochloric acid is used. The acid solution is preferably heated to about 40–60° C., more preferably about 40–45° C., and the cyano intermediate is slowly added. As the cyano intermediate is added, methylene chloride is distilled off. The reaction is complete after about 3–4 hours at 50–52° C., at which point the methylene chloride is completely eliminated. The reaction mixture is cooled and the carboxamide intermediate is isolated by filtration. The obtained 1H-imidazo[4,5-c]quinoline 4-carboxamide intermediate has a high purity, i.e., at least 99% as measured by HPLC, and is obtained in good yield, i.e., about 71–71% with respect to the 1H-imidazo[4,5-c]quinoline N-oxide. Thus, the 1H-imidazo[4,5-c]quinoline 4-hydroxy impurity formed during the cyanation reaction in an amount of about 5–6%, is almost completely eliminated.

To prepare a 1H-imidazo[4,5-c]quinoline 4-amine, an alkali or alkaline earth metal salt of a hypohalous acid (HOX) such as NaOBr or NaOCl and a strong base such as an alkali or alkaline earth metal oxide or hydroxide, for example, NaOH, KOH or MgO, is reacted with a 1H-imidazo[4,5-c]quinoline 4-carboxamide intermediate, which undergoes a Hofmann rearrangement to degrade the amide group and form an amine at the corresponding position of the quinoline ring system. A Hofmann rearrangement is a known reaction described in Morrison and Boyd's *Organic Chemistry*, sixth edition, p. 838–843, which is incorporated by reference herein. The reaction takes place in a suitable solvent. A preferred solvent is a mixture of 1,2-dimethoxyethane and water. The reaction preferably occurs at a temperature of between 50–52° C. for a period of about 2 hours. After the reaction is complete, the suspension is acidified and most of the 1,2-dimethoxyethane is distilled off and replaced with water. A crude 1H-imidazo[4,5-c]quinoline 4-amine salt is recovered.

The crude Imiquimod is purified by techniques known in the art, including conventional crystallization and/or recrystallization.

One reaction scheme that may be used to make 1H-imidazo[4,5-c]quinoline-4-amines of formula (I) is shown below:

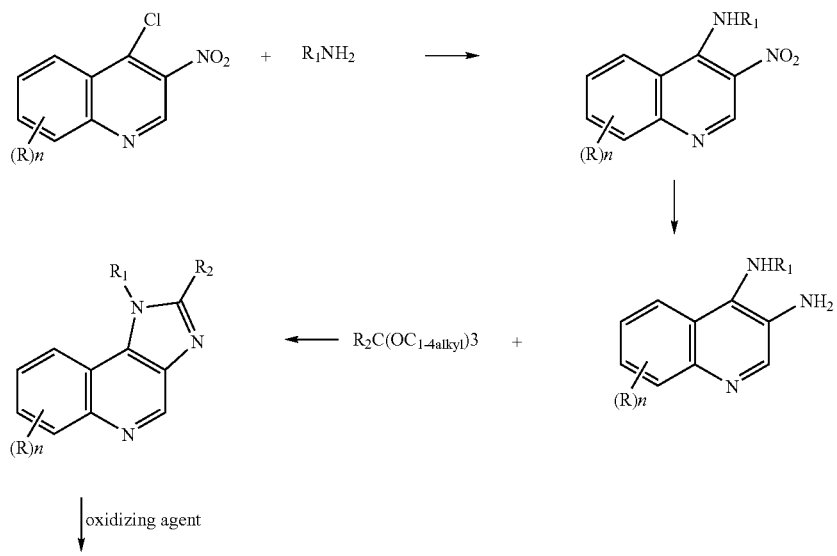

-continued

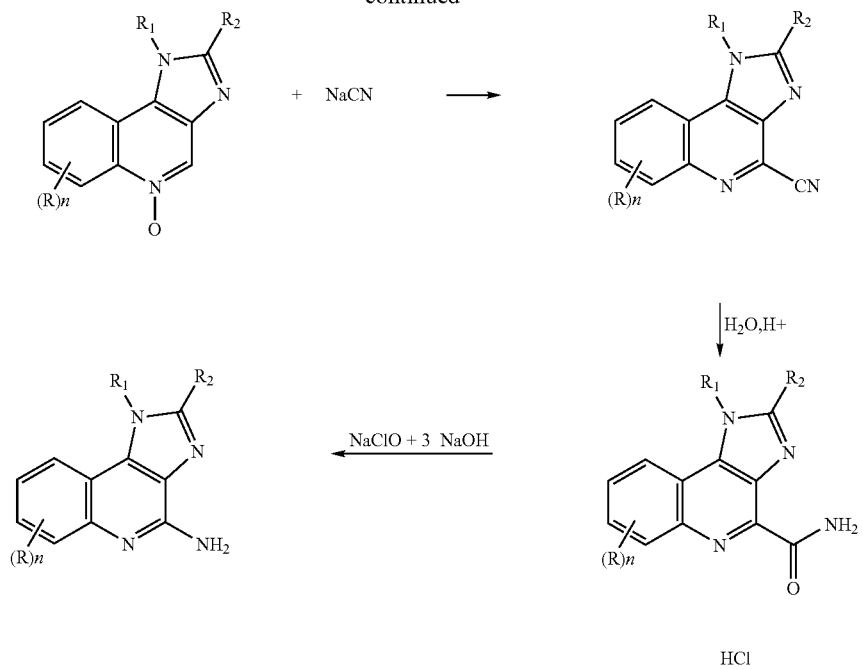

The present invention is illustrated in further detail with reference to the following non-limiting examples.

EXAMPLE 1

Preparation of 4-isobutyl-3-nitro quinoline 4-chloro-3-nitro-quinoline is reacted with isobutyl amine in the presence of triethanolamine (TEA) at between −10 and +15° C. in toluene, while excluding moisture. After washing and phase separation, the organic solution is ready for the next step.

EXAMPLE 2

Preparation of 4-isobutyl-3-amino quinoline

The nitroxide group on the 4-isobutyl-3-nitro quinoline produced in Example 1 is reduced by catalytic reduction using toluene as solvent, Pd/C 5% (50% wet) as catalyst, at 40–45° C. and atmospheric pressure to produce 4-isobutyl 3-amino quinoline. The rate of reaction depends on efficiency of stirring. After catalyst filtration the solution is ready for the next step.

EXAMPLE 3

Preparation of 1-isobutyl-1H-imidazo[4,5-c]quinoline

The cyclization of 4-isobutyl 3-amino quinoline produced in Example 2 is carried out in toluene at 102–110° C. using TEOF (triethyl orthoformate) and 20% moles of formic acid to increase the rate of reaction, to produce 1-isobutyl-1H-imidazo[4,5-c]quinoline. Before addition of TEOF, in order to prevent its hydrolysis, it is necessary to remove water formed during the catalytic reduction by azeotropic distillation. A mixture of ethanol and toluene is distilled during the reaction to maintain the internal temperature at 102–110° C.

EXAMPLE 4

Preparation of 1-isobutyl-1H-imidazo[4,5-c]quinoline N-oxide

The oxidation of 1-isobutyl-1H-imidazo[4,5-c]quinoline produced in Example 3 is carried out in toluene at 40–45° C. using peracetic acid as oxidant to produce 1-isobutyl-1H-imidazo[4,5-c]quinoline N-oxide. The product is isolated by filtration after addition of a sodium sulfate solution and ammonium hydroxide.

EXAMPLE 5

Preparation of 1-isobutyl-1H-imidazo[4,5-c]quinoline-4-cyano 300 ml water and 91.1 g (1.859 moles) sodium cyanide are loaded into a 2000 ml reactor and stirred at 20–25° C. until the sodium cyanide is completely dissolved. Then 900 ml of methylene chloride and 155.7 g (0.6216 moles) of 1-isobutyl-1H-imidazo[4,5-c]quinoline-N-oxide are added. The suspension is stirred at 25° C. for 10 minutes and then cooled to −5° C. The temperature is maintained at between −5 and −1° C. as 92.6 g (0.6589 moles) benzoyl chloride is dropped into the reactor over a period of about 1 hour and 40 minutes. This mixture is stirred at 0° C. for about 30 minutes and a sample is taken. HPLC analysis should show that there is no starting material, 92% target product and 5.48% 4-hydroxy derivative. If there is unreacted starting material present, benzoyl chloride is added in an amount equal to the amount of reagent left. Next, the mixture is heated to 20° C. and 200 ml water and 3 g tetrabutyl ammonium bromide is added. The phases are separated such that the organic layer is about 990 ml and the aqueous layer is about 620 ml. The organic layer is washed with 200 ml 10% $Na_2CO_3$ and the phases are separated such that the organic layer is about 965 ml and the aqueous layer is about 210 ml. A 200 ml solution of 5% NaClO is added very slowly to the organic layer while maintaining the temperature at 20–25° C. The mixture is stirred and after about 5 minutes the phases are separated such that the organic layer is about 940 ml and the aqueous layer is about 210 ml. The organic layer is washed with 200 ml water and the phases are separated. The organic layer is concentrated under vacuum until a volume of about 350 ml is obtained. The solution, maintained at 30–32° C. to avoid crystallization, is used in the next step.

EXAMPLE 6

Preparation of 1-isobutyl-1H-imidazo[4,5-c]quinoline-4-carboxamide 832 g (6.84 moles) of 30% hydrochloric acid is loaded into a 2000 ml reactor and heated to 50° C. The jacket temperature is maintained at 60° C. as the solution from example 5 (350 ml of 155.6 g (0.6216 moles) of 1H-imidazo[4,5-c]quinoline-4-cyano) is dropped into the reactor, distilling off methylene chloride. During the addition, the internal temperature is 40–45° C. and hydrochloric gas is given off. At the end of the addition, the internal temperature rises to about 50–52° C. and methylene chloride is completely eliminated. The internal temperature is maintained at about 50–52° C. for about 3.5 hours and a solid precipitates. After 3.5 hours a sample is taken. There should be a complete transformation of starting material. The suspension is cooled to 0° C. and after 2 hours the solid if filtered and washed 4 times with 40 ml water and 4 times with 40 ml isopropanol. The solid is dried at 50° C. under vacuum for 10 hours at which time 152.8 g of 1-isobutyl-1H-imidazo[4,5-c]quinoline-4-carboxamide hydrochloride is obtained. HPLC analysis shows that the solid is 97.7% pure and the yield based on the amount of 1-isobutyl-1H-imidazo[4,5-c]quinoline N-oxide starting material is 70.2%.

EXAMPLE 7

HPLC analysis of 1-isobutyl-1H-imidazo[4,5-c]quinoline-4-carboxamide

The purity of four samples of solid 1-isobutyl-1H-imidazo[4,5-c]quinoline-4-carboxamide, made according to the invention, was measured by HPLC analysis. The HPLC parameters were as follows:

| APPARATUS: | HPLC Perkin Elmer Series 200 with autosamp,er and diode array detector or equivalent. |
|---|---|
| REAGENTS: | Acetonitrile HPLC grade |
| | Potassium phosphate monobasic RPE-ACS for analysis |
| | Phosphoric acid RPE-ACS for analysis |
| MOBILE PHASE: | aqueous phase: prepare a pH 2.7 phosphate buffer 0.02M as follows: dissolve 2.72 g of potassium phosphate monobasic in 1000 mL of HPLC grade deionized water, adjust the pH to 2.7 ± 0.02 with 15% (wt/v) phosphoric acid. Filter on a 0.45 μm filter. |
| | Organic phase: acetonitrile |
| GRADIENT TIMETABLE: | Cumulated time (min)  % aqueous phase  % organic phase |
| | 0   80   20 |
| | 12   64   36 |
| | 19   40   60 |
| | 27   40   60 |
| | Equilibration time:   8 min |
| TEMPERATURE: | 30° C. |
| COLUMN: | ALLTIMA C18 5 micron, 150 mm × 4.6 mm (from ALLTECH) |
| FLOW: | 1.0 mL/min |
| WAVELENGTH: | 210 nm |
| INJECTION: | 5 microliters |

The HPLC results for the four samples are summarized in Table I:

TABLE I

| Sample no. | IMI-Amide* | IMI-OH** | IMI-CN*** |
|---|---|---|---|
| 1 | 99.08 | 0.61 | n.d. |
| 2 | 99.47 | 0.36 | n.d. |
| 3 | 99.25 | 0.44 | n.d. |
| 4 | 99.63 | 0.24 | 0.03 |

*1-isobutyl-1H-imidazo[4,5-c]quinoline-4-carboxamide
**1H-imidazo[4,5-c]quinoline 4-hydroxy impurity
***1-isobutyl-1H-imidazo[4,5-c]quinoline-4-cyano

EXAMPLE 9

Preparation of 1-isobutyl-1H-imidazo[4,5-c]quinoline-4-amine 500 ml (433.5 g) of 1,2dimethoxyethane and 50 g (0.164 moles) of 1-isobutyl-1H-imidazo[4,5-c]quinoline 4-carboxamide hydrochloride (99.08%) are loaded into a 1000 ml reactor. The reactor temperature is maintained at between about 27–28° C. as 21.7 g (0.57 moles) of 30% sodium hydroxide is added. Then a solution of 104.35 g (0.18 moles) of sodium hypochlorite(12.88% as NaClO) in 54.3 g 30% NaOH is added. The suspension is stirred at 27–28° C. for about 1 hour. The suspension is heated to 50–52° C. and this temperature is maintained for about 2 hours at which time a sample is taken. If the intermediate is less than 0.5%, the suspension is cooled 40° C. and as the temperature is maintained below 50° C., 75 g of 37% HCl is slowly dropped in. Carbon dioxide gas is evolved during the addition. Most of the 1,2-dimethoxyethane is distilled under vacuum with the external temperature at 52° C. until the residual volume is 450 ml. The internal temperature is maintained at 50–52° C. as 125 ml of water is added. The suspension is further distilled under vacuum until the residual volume is 530 ml. The suspension is stirred at 50–52° C. for 30 minutes and filtered at 50–52° C. The solid is washed twice with 50 ml of cool water and then twice with 50 ml (79 g) of acetone. The solid is dried under vacuum at 50° C. for 10 hours. 41.54 g of Imiquimod HCl is obtained at a yield of 91.5%.

EXAMPLE 10

Purification of 1-isobutyl-1H-imidazo[4,5-c]quinoline-4-amine 100 ml water and 10 g crude Imiquimod HCl are loaded into a 250 ml reactor. The mixture is heated to 85–90° C. to obtain a solution. 0.2 g sodium hydrosulfite is added and the solution turns from orange to yellow. 1 g of charcoal is added and after 10 minutes at 90–95° C. the charcoal is filtered off and the cake is washed with 10 ml of hot water. To the pale yellow solution obtained, 1 g of charcoal is added and stirred for 10 minutes at 90–95° C. The charcoal is filtered off and the cake is washed with 10 ml hot water. To the colorless solution obtained, 3 g $NH_4OH$ ($NH_3$ 26%) is added at 80° C. The white suspension obtained is cooled to 20° C. and filtered. The cake is washed three times with 10 ml water. No chloride should be detected by silver nitrate during the washes. The solid is dried under vacuum at 50° C. for 10 hours. A 7 g solid is obtained and the yield is 80.5%.

Having thus described the invention with reference to particular preferred embodiments and illustrated it with examples, those of skill in the art may appreciate modifications to the invention as described and illustrated that do not depart from the spirit and scope of the invention as disclosed in the specification.

What is claimed is:

1. A compound of formula (II) and salts thereof,

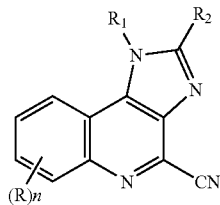

(II)

wherein
  $R_1$ is selected from the group consisting of: hydrogen; a straight or branched chain alkyl of one to 10 carbon atoms, optionally substituted with a substituent selected from the group consisting of lower alkyl, cycloalkyl of 3 to 6 carbon atoms, wherein said cycloalkyl is optionally substituted with a lower alkyl group; straight or branched chain alkenyl of 2 to 10 carbon atoms, wherein the olefinic unsaturation in the alkenyl group is at least one carbon atom removed from the 1-nitrogen, and wherein the straight or branched chain alkyl is optionally substituted with a substituent selected from the group consisting of lower alkyl, cycloalkyl of 3 to 6 carbon atoms, wherein said cycloalkyl is optionally substituted with a lower alkyl group; hydroxyalkyl of one to six carbon atoms; acyloxyalkyl wherein the acyloxy moiety is alkanoyloxy of two to four carbon atoms or benzoyloxy and the alkyl moiety contains one to six carbon atoms; benzyl; (phenyl)ethyl; and phenyl, wherein said benzyl, (phenyl)ethyl and phenyl substituents are optionally substituted on the benzene ring by one or two moieties independently selected from the group consisting of lower alkyl, lower alkoxy, and halogen, with the proviso that when the benzene ring is substituted by two such moieties, then the moieties together contain more than 6 carbon atoms;
  $R_2$ is selected from the group consisting of: hydrogen; straight or branched chain alkyl containing one to eight carbon atoms; benzyl; (phenyl)ethyl; and phenyl, wherein said benzyl, (phenyl)ethyl and phenyl substituents are optionally substituted on the benzene ring by one or two moieties independently selected from the group consisting of lower alkyl, lower alkoxy, and halogen, with the proviso that when the benzene ring is substituted by two such moieties, then the moieties together contain more than 6 carbon atoms;
  R is independently selected from the group consisting of: alkoxy of one to four carbon atoms; alkyl of one to four carbon atoms; and halogen; and
  n is an integer from 0 to 2, with the proviso that if n is 2, then said groups together contain no more than 6 carbon atoms.

2. A compound of claim 1, wherein $R_1$ is isobutyl, $R_2$ is hydrogen, and n is 0.

3. A process for preparing a 1H-imidazo[4,5-c]quinoline 4-cyano compound of formula (II) and salts thereof, comprising reacting a compound of formula (III) with an alkali metal cyanide in a suitable solvent to form a reaction mixture:

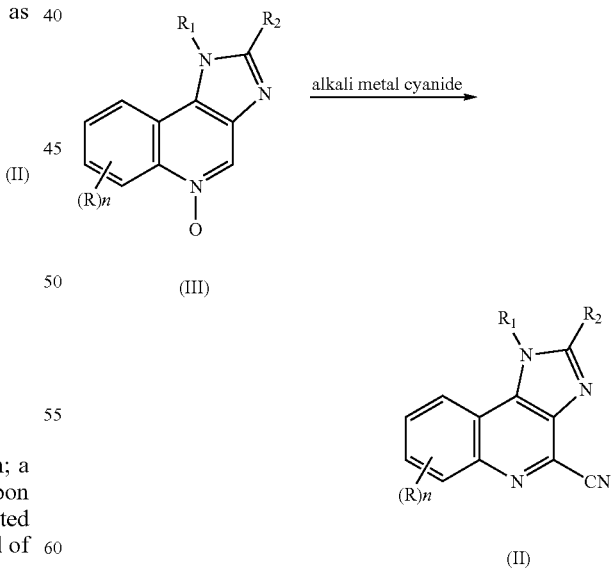

wherein
  $R_1$ is selected from the group consisting of: hydrogen; a straight or branched chain alkyl of one to 10 carbon atoms, optionally substituted with a substituent selected from the group consisting of lower alkyl, cycloalkyl of 3 to 6 carbon atoms, wherein said cycloalkyl is optionally substituted with a lower alkyl group; straight or branched chain alkenyl of 2 to about 10 carbon atoms, wherein the olefinic unsaturation in the alkenyl group is at least one carbon atom removed from the 1-nitrogen, and wherein the straight or branched chain alkyl is optionally substituted with a substituent selected from the group consisting of lower alkyl, cycloalkyl of 3 to 6 carbon atoms, wherein said cycloalkyl is optionally substituted with a lower alkyl group; hydroxyalkyl of one to six carbon atoms; acyloxyalkyl wherein the acyloxy moiety is alkanoyloxy of two to four carbon atoms or benzoyloxy and the alkyl moiety contains one to six carbon atoms; benzyl; (phenyl)ethyl; and phenyl, wherein said benzyl, (phenyl)ethyl and phenyl substituents are optionally substituted on the benzene ring by one or two moieties independently selected from the group consisting of lower alkyl, lower alkoxy, and halogen, with the proviso that when the benzene ring is substituted by two such moieties, then the moieties together contain more than 6 carbon atoms;

$R_2$ is selected from the group consisting of: hydrogen; straight or branched chain alkyl containing one to eight carbon atoms; benzyl; (phenyl)ethyl; and phenyl, wherein said benzyl, (phenyl)ethyl and phenyl substituents are optionally substituted on the benzene ring by one or two moieties independently selected from the group consisting of lower alkyl, lower alkoxy, and halogen, with the proviso that when the benzene ring is substituted by two such moieties, then the moieties together contain more than 6 carbon atoms;

R is independently selected from the group consisting of: alkoxy of one to four carbon atoms; alkyl of one to four carbon atoms; and halogen; and n is an integer from 0 to 2, with the proviso that if n is 2, then said groups together contain no more than 6 carbon atoms.

4. The process of claim 3, wherein $R_1$ is isobutyl, $R_2$ is hydrogen, and n is 0.

5. The process of claim 3, wherein the reaction is carried out in the presence of an organic acid halide.

6. The process of claim 5, wherein the organic acid halide is benzoyl chloride.

7. The process of claim 3, wherein the solvent is a mixture of methylene chloride and water.

8. The process of claim 3, wherein the ratio of alkali metal cyanide to compound (III) is from about 3:1.

9. The process of claim 3, wherein the reaction is carried out at a temperature of between about −5 to +5° C.

10. The process of claim 5, wherein the organic acid halide is added to the reaction mixture over a period of from about 1 to about 3 hours.

11. The process of claim 3, wherein the reaction mixture comprises an aqueous phase and an organic phase.

12. The process of claim 11, further comprising separating the organic phase from the aqueous phase and washing and concentrating the organic phase.

13. The process of claim 11, further comprising adding t-butyl ammonium bromide to the reaction mixture.

14. A process for preparing a compound of formula (I) or a pharmaceutically acceptable acid addition salt thereof:

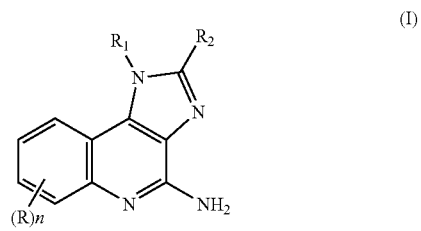

comprising the step of reacting a compound of formula (III) with an alkali metal cyanide in a suitable solvent to form a reaction mixture:

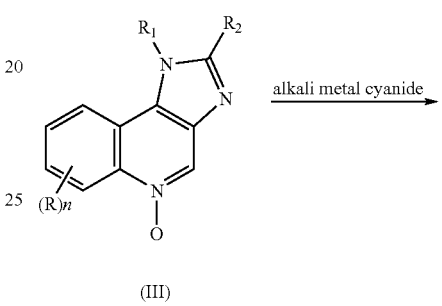

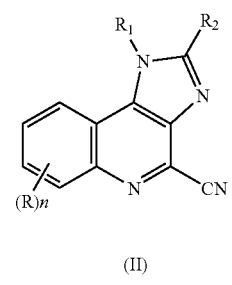

wherein $R_1$ is selected from the group consisting of: hydrogen; a straight or branched chain alkyl of one to 10 carbon atoms, optionally substituted with a substituent selected from the group consisting of lower alkyl, cycloalkyl of 3 to 6 carbon atoms, wherein said cycloalkyl is optionally substituted with a lower alkyl group; straight or branched chain alkenyl of 2 to 10 carbon atoms, wherein the olefinic unsaturation in the alkenyl group is at least one carbon atom removed from the 1-nitrogen, and wherein the straight or branched chain alkyl is optionally substituted with a substituent selected from the group consisting of lower alkyl, cycloalkyl of 3 to 6 carbon atoms, wherein said cycloalkyl is optionally substituted with a lower alkyl group; hydroxyalkyl of one to six carbon atoms; acyloxyalkyl wherein the acyloxy moiety is alkanoyloxy of two to four carbon atoms or benzoyloxy and the alkyl moiety contains one to six carbon atoms; benzyl; (phenyl)ethyl; and phenyl, wherein said benzyl, (phenyl)ethyl and phenyl substituents are optionally substituted on the benzene ring by one or two moieties independently selected from the group consisting of lower alkyl, lower alkoxy, and halogen, with the proviso that when the benzene ring is substituted by two such moieties, then the moieties together contain more than 6 carbon atoms;

$R_2$ is selected from the group consisting of: hydrogen; straight or branched chain alkyl containing one to about eight carbon atoms; benzyl; (phenyl)ethyl; and phenyl, wherein said benzyl, (phenyl)ethyl and phenyl substituents are optionally substituted on the benzene ring by one or two moieties independently selected from the group consisting of lower alkyl, lower alkoxy, and halogen, with the proviso that when the benzene ring is substituted by two such moieties, then the moieties together contain more than 6 carbon atoms;

R is independently selected from the group consisting of: alkoxy of one to four carbon atoms; alkyl of one to four carbon atoms; and halogen; and n is an integer from 0 to 2, with the proviso that if n is 2, then said groups together contain no more than 6 carbon atoms.

* * * * *